(12) United States Patent
Pizzutillo

(10) Patent No.: US 8,840,576 B2
(45) Date of Patent: Sep. 23, 2014

(54) BRACE INSTALLATION DEVICE

(76) Inventor: Richard Pizzutillo, Newton, NJ (US)

( * ) Notice: Subject to any disclaimer, the term of this patent is extended or adjusted under 35 U.S.C. 154(b) by 0 days.

(21) Appl. No.: 13/430,620

(22) Filed: Mar. 26, 2012

(65) Prior Publication Data

US 2013/0253398 A1    Sep. 26, 2013

(51) Int. Cl.
*A61F 5/00*    (2006.01)

(52) U.S. Cl.
USPC ............................................................ 602/19

(58) Field of Classification Search
USPC ............ 602/19; 128/874–875; 606/54, 56, 59
See application file for complete search history.

(56) References Cited

U.S. PATENT DOCUMENTS

| 4,098,269 A * | 7/1978 | Judet ............................... 606/54 |
| 8,287,537 B2 * | 10/2012 | Dinkler, II ..................... 606/59 |
| 2005/0251136 A1 * | 11/2005 | Noon et al. ..................... 606/56 |

* cited by examiner

*Primary Examiner* — Michael A. Brown
(74) *Attorney, Agent, or Firm* — Barbara V Maurer

(57) ABSTRACT

Thus this invention relates to a device, preferably hand held, designed for the installation of an adjustable tension, stretchable, brace that allows equal tension throughout the entire width of the brace during installation. The device of the invention is used in conjunction with pins that are positioned at either end of the brace and are removed when the brace is secured in position.

7 Claims, 7 Drawing Sheets

BRACE INSTALLATION DEVICE

This application claims the benefit of U.S. Provisional Application No. 61/466,699, filed Mar. 23, 2011.

This invention relates to a device to install and hold in place a tension bandage or wrap wherein there is even tension throughout the area of the brace.

BACKGROUND OF THE INVENTION

Abdominal and lumbar braces are well known in the art. They are used, for example, to help maintain proper posture and to provide support for the torso, either abdominal support, support after surgery or back support. In general they are comprised of an elastic-like swath of material that is secured around the mid-section of a person's body. The material is generally several inches wide, ranging from about 6 inches to about 15 or more inches.

When the brace is applied to the torso, it is generally advantageous to have the tension of the brace similar across the width of the brace. This is often accomplished by using a hook and pile type fastener. Depending on the type and structure of the brace a patient applying the brace can have difficulty applying consistent tension across the width of the brace when placing it around the body.

In some cases, the brace is constructed of firmer or less elastic material. The brace can be closed and held in place by a tapered end. However this type of closure is not appropriate for braces which are constructed to require even tension across the brace material when applying.

Thus there remains a need for some type of assist to the patient or assistant other person aiding the patient when applying the brace.

SUMMARY OF THE INVENTION

Thus this invention relates to a device, preferably hand held, designed for the installation of an adjustable tension, stretchable, brace that allows equal tension throughout the entire width of the brace during installation. The device of the invention is used in conjunction with pins that are positioned at either end of the brace.

DESCRIPTION OF INVENTION

Figure 1:
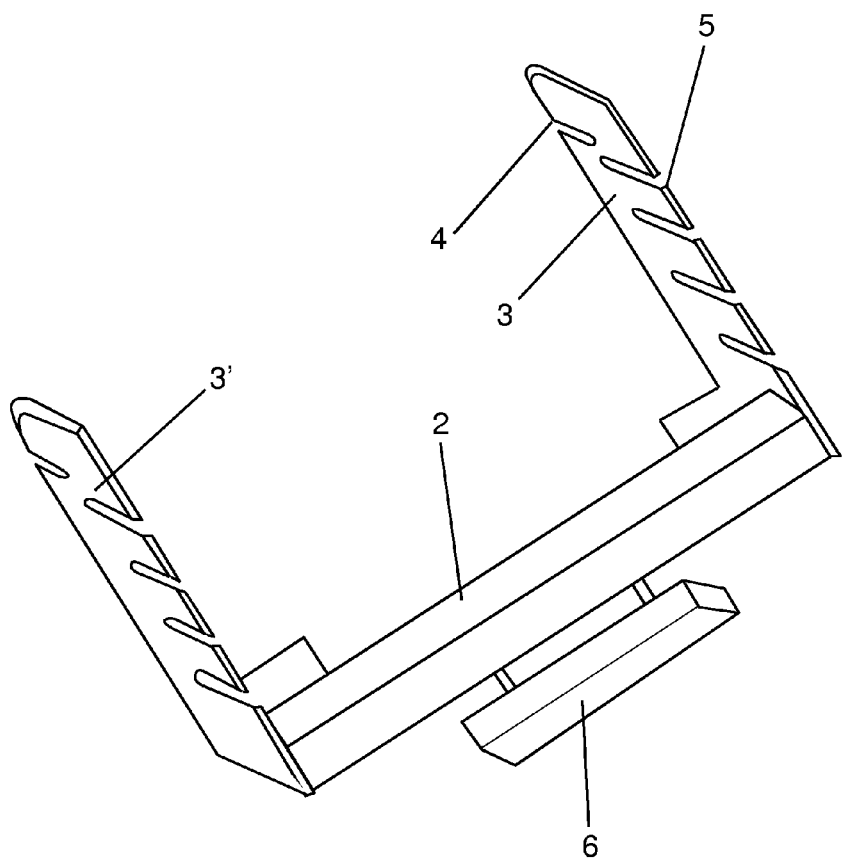
FIG. 1 shows a schematic embodiment of the device of the invention in an open position.
Figure 2:
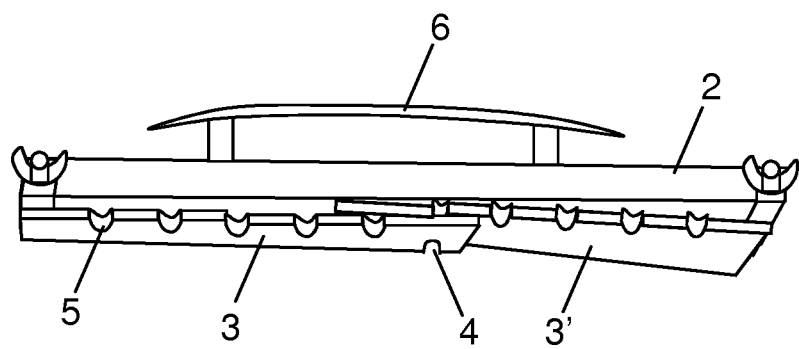
FIG. 2 shows an embodiment of the invention in a closed position.
Figure 3:
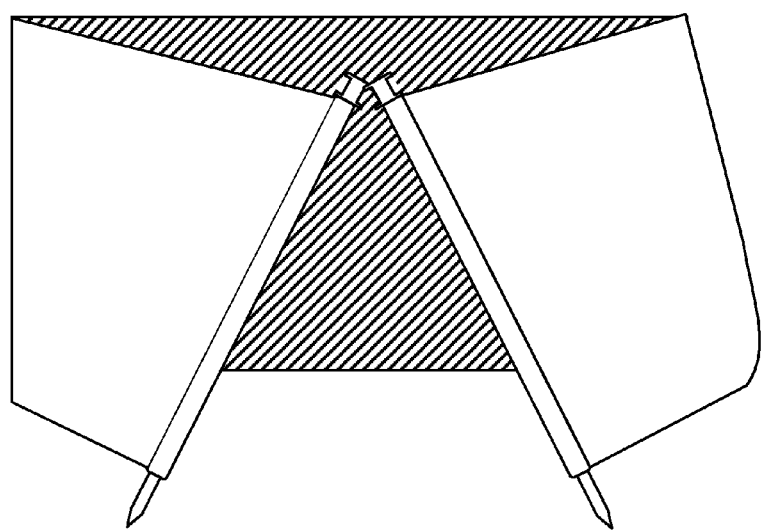
FIG. 3 shows a brace with pins attached and ready for installation.

The invention can be best described by reference to the Figures. Referring to FIG. 1 the device 1 is comprised of a bar 2 to which are attached on either end sidebars 3 and 3'. The side bars 3 and 3' have multiple slots 4 and 5 which are designed to accept the ends of pins that have been inserted in both ends of a brace (as shown in FIG. 3). Preferably bar 2 has a handle 6 to enable easy use of the device. The sidebars 3 and 3' are attached to bar 2 either immovably or by a folding mechanism so that the sidebars can be folded longitudinally along bar 2 for storage, as seen in FIG. 2.

FIG. 3 shows a photograph of pins of the invention inserted into a brace through pockets on either end of the brace, in preparation for using the device of the invention for installation.

Figure 4:
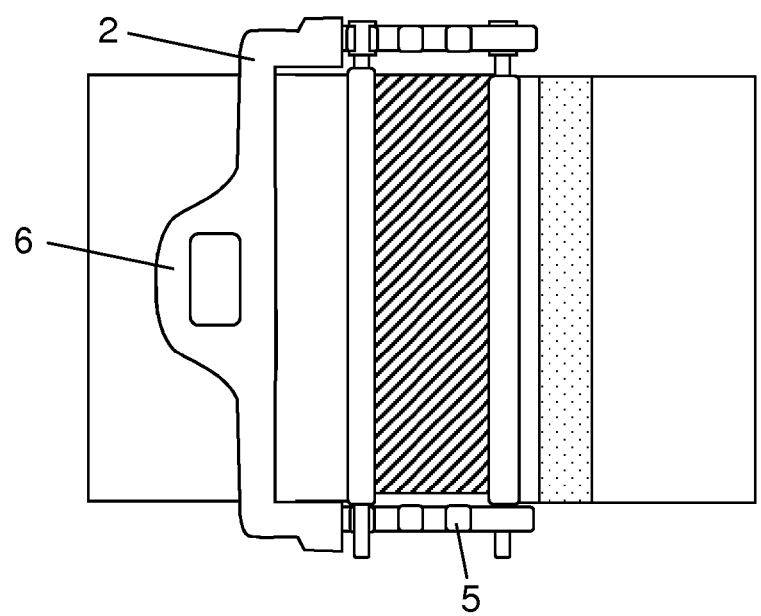
FIG. 4 shows an embodiment of the invention attached to a brace and positioned on the body ready for installation.
Figure 5:
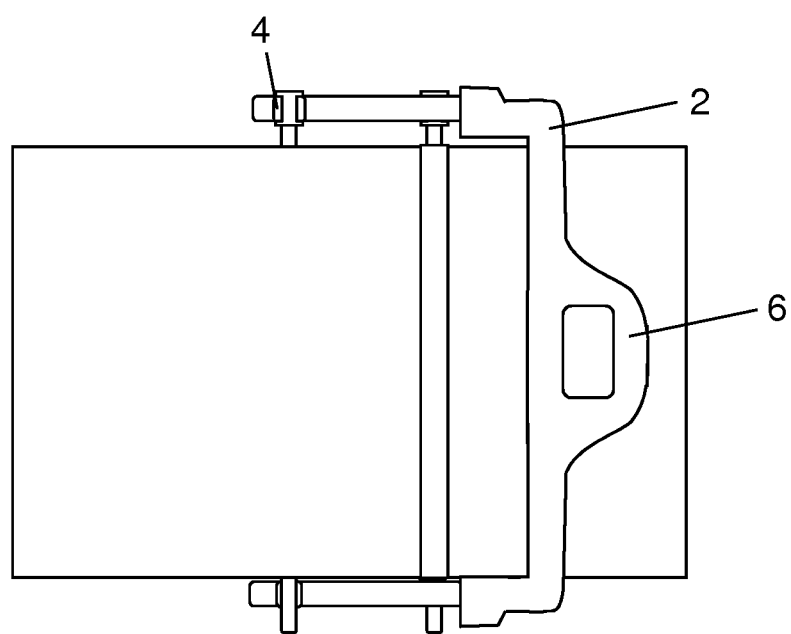
FIG. 5 shows installation of a brace with the device of the invention where the brace has been installed but is still attached to the device of the invention.
Figure 6:
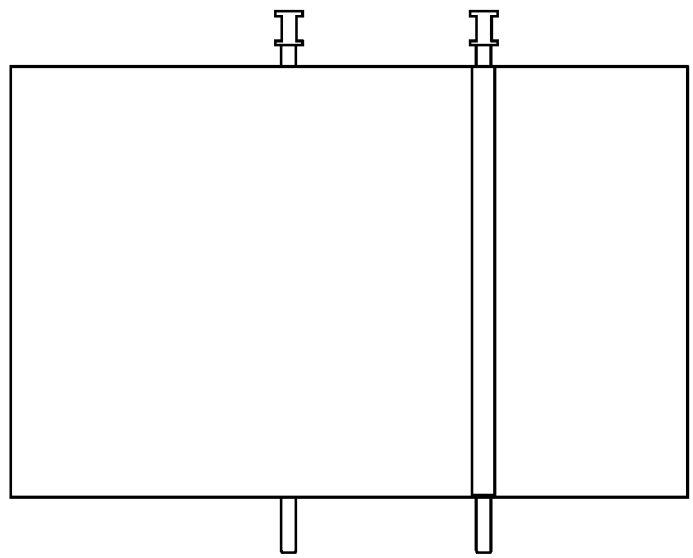
FIG. 6 shows installation of a brace where the device has been removed but pins still remain in the brace.
Figure 7:
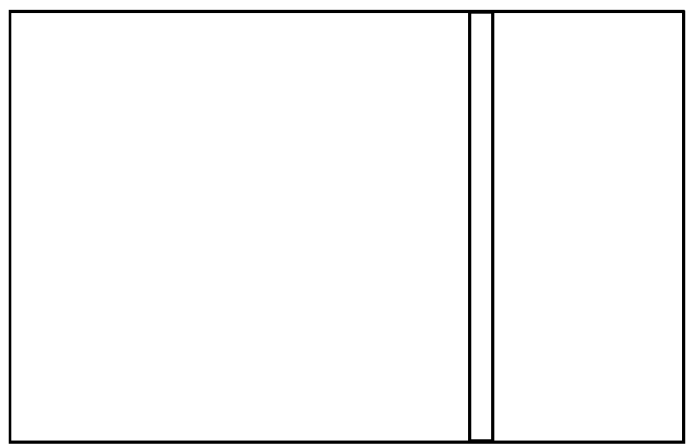
FIG. 7 shows a completed installation of a brace where the pins have been removed.

In use, in one embodiment of the invention, the brace is put in position around the midsection of the body and the pins are hooked to the machined slots in the device, with one pin being hooked into slot 4 and the other being hooked into the appropriate slot 5, as shown in FIG. 4. The device is then pivoted on the pin in slot 4 to draw the edges of the brace so that they overlap and can be fastened together, as shown in FIG. 5. Once the edges of the brace are fastened together, first the device is detached from the pins, leaving the brace installed with the pins remaining. This is shown if FIG. 6. Finally the pins are removed and the brace is completely installed as shown in FIG. 7.

The device of the invention can be constructed of any material with sufficient strength to cause the needed tension in the brace without bending, preferably metal, such as steel or aluminum or plastic, more preferably plastic such as polyoxymethylene polymer, also known as acetal homopolymer. It is within the scope of the invention that more than one material can be used in the same device.

The pins are constructed of a material that will not bend during installation of the brace, preferably metal or plastic, more preferably metal, such as hardened steel or graphite. Optionally, the pins have a stop on one end so that they will not slide through the pocket in the brace holding the pin and/or slide through the slot on the device. They are longer than the device is wide, so that for example if the device is about 12 inches wide, the pins could be up to 14 inches long.

The device is designed to be slightly wider than the brace to be installed so that the sidebars do not interfere with the pivoting action during installation. The device can be any width necessary to accept a brace, and preferably a brace that is commercially available such as one that is up to about 12 or 15 inches wide or as narrow as about 6 inches wide. In on embodiment of the invention, for example the bar 2 is about 12 inches long and the sidebars 3 and 3' are about 8 inches long.

The distance between the slots 5 on the sidebars can be adjusted according to the variability needed with the type of brace being applied, preferably as suggested by an attending physician. Preferably in a common usage they are between from about 0.0 and 1.5 inches apart. In one embodiment of the invention the distance between the slots 5 is about 1 inch. The number of slots can range from about one or two up to eight or more, depending on the spacing between them and the amount of overlap needed. The width of the slot is designed to be wide enough to accommodate a pin. In one embodiment of the invention the slots are about 3/16 of an inch wide. Preferably, the innermost part of the slot is shaped to hold a pin used with the invention. In one embodiment the bottom of the slot is shaped like a semi-circle to accommodate a cylindrical pin. However other shapes such as a square pin and corresponding slot could also be used.

The device of the invention can advantageously be used for application of any brace used in the mid-section of the body, such as, for example, a back brace, a mid-body compression support garment, a post-liposuction/tummy tuck compression garment binder, a maternity support garment, abdominal binder, hernia belt, plastic surgery binder or surgery dressing retainer.

It is also contemplated within the invention that the device could be used to apply any type of binding, tape or bandage that could be more advantageously used if applied with even tension, such as, for example a pressure bandage such as an "ace-type" bandage.

Also contemplated within the invention is an installation kit that contains the device of the invention along with pins of the corresponding size and shape. This is advantageous for a patient using the device because all the necessary parts to use the invention are contained in a single place.

The invention has been described with particular reference to the preferred embodiments without limit thereto. One of skill in the art would readily appreciate additional modifications and embodiments which are not specifically stated but which are within the scope of the invention as set forth in the claims appended hereto.

The invention claimed is:

1. A device for the installation of a brace which comprises
   a primary bar; and
   a sidebar attached on each end of the primary bar;
   wherein the primary bar is attached to the sidebars with hinges; and
   wherein each sidebar has from one to eight slots on one side and one slot on the distal end on the opposite side.

2. The device of claim 1 which is constructed from plastic.

3. The device of claim 2 wherein the plastic is polyoxymethylene homopolymer.

4. The device of claim 1 which is constructed from hardened steel.

5. The device of claim 1 which has a handle on the primary bar.

6. The device of claim 1 wherein the sidebars are constructed from aluminum.

7. A kit for the installation of a brace which comprises
   a device having a primary bar and a sidebar attached on each end of the primary bar;
   wherein each sidebar has from one to eight slots on one side and one slot on the distal end on the opposite side; and
   at least 2 pins for attaching a brace to the device.

* * * * *